(12) United States Patent
Wroblesky et al.

(10) Patent No.: US 10,525,140 B2
(45) Date of Patent: Jan. 7, 2020

(54) COMPOSITE CONTAINING POLY(GLYCEROL SEBACATE) FILLER

(71) Applicant: THE SECANT GROUP, LLC, Telford, PA (US)

(72) Inventors: Kayla Wroblesky, Schwenksville, PA (US); Carissa Smoot, Harleysville, PA (US); Peter D. Gabriele, Frisco, TX (US); Jeremy J. Harris, Buckingham, PA (US); Charles Brendan Nicholson, Coopersburg, PA (US); Steven Lu, Ambler, PA (US)

(73) Assignee: THE SECANT GROUP, LLC, Telford, PA (US)

( * ) Notice: Subject to any disclaimer, the term of this patent is extended or adjusted under 35 U.S.C. 154(b) by 0 days.

(21) Appl. No.: 15/442,055

(22) Filed: Feb. 24, 2017

(65) Prior Publication Data

US 2017/0246316 A1  Aug. 31, 2017

Related U.S. Application Data

(60) Provisional application No. 62/299,595, filed on Feb. 25, 2016.

(51) Int. Cl.
| | |
|---|---|
| *A61K 47/59* | (2017.01) |
| *A61K 47/34* | (2017.01) |
| *C08J 3/12* | (2006.01) |
| *C08G 63/12* | (2006.01) |
| *C08L 67/00* | (2006.01) |
| *C08K 3/013* | (2018.01) |

(52) U.S. Cl.
CPC ............ *A61K 47/593* (2017.08); *A61K 47/34* (2013.01); *C08G 63/12* (2013.01); *C08J 3/12* (2013.01); *C08K 3/013* (2018.01); *C08L 67/00* (2013.01); *C08J 2367/02* (2013.01)

(58) Field of Classification Search
None
See application file for complete search history.

(56) References Cited

U.S. PATENT DOCUMENTS

| | | | |
|---|---|---|---|
| 6,017,566 A | 1/2000 | Bunczek et al. | |
| 6,444,782 B1 | 9/2002 | Hamlin | |
| 7,722,894 B2 | 5/2010 | Wang et al. | |
| 7,807,211 B2 * | 10/2010 | Hossainy ............... | A61F 2/82 427/2.1 |
| 8,716,410 B2 | 5/2014 | Venkatraman et al. | |
| 2003/0118692 A1 | 6/2003 | Wang et al. | |
| 2004/0039440 A1 | 2/2004 | Elmaleh | |
| 2005/0133046 A1 | 6/2005 | Becker et al. | |
| 2005/0169958 A1 | 8/2005 | Hunter et al. | |
| 2006/0009839 A1 | 1/2006 | Tan | |
| 2007/0023974 A1 | 2/2007 | Wu | |
| 2009/0082840 A1 | 3/2009 | Rusk et al. | |
| 2009/0214373 A1 | 8/2009 | Stinson et al. | |
| 2010/0094404 A1 | 4/2010 | Greenhalgh et al. | |
| 2011/0038910 A1 | 2/2011 | Faucher et al. | |
| 2011/0142790 A1 | 6/2011 | Chen | |
| 2012/0143347 A1 | 6/2012 | Wang et al. | |
| 2015/0320542 A1 | 11/2015 | Gabriele et al. | |
| 2015/0344618 A1 | 12/2015 | Nicholson et al. | |
| 2016/0046832 A1 | 2/2016 | Wroblesky et al. | |
| 2016/0242895 A1 | 8/2016 | Matheny | |
| 2016/0251540 A1 | 9/2016 | Nicholson et al. | |

FOREIGN PATENT DOCUMENTS

| | | |
|---|---|---|
| CN | 104629023 | 5/2015 |
| GB | 1419128 | 12/1975 |
| JP | H03047870 | 2/1991 |

OTHER PUBLICATIONS

Rai et al., "Synthesis, properties and biomedical applications of poly(glycerol sebacate) (PGS): A review", Progress in Polymer Science, 2012, vol. 37, pp. 1051-1078 (Year: 2012).*
Sun, ZJ et. al., Materials Science and Engineering, The influence of lactic acid on the properties of Poly (glycerol-sebacate-lactic acid),2009, p. 178-182, C29.
Wang, Yadong et. al. A Tough Biodegradable Elastomer,vol. 20, p. 602-606, Jun. 2002, Nature Publishing Group.
Gao, Jin et. al., Macroporous Elastomeric Scaffolds with Extensive Micropores for Soft Tissue Engineering, Wallace H. Coulter Department of Biomedical Engineering, Georgia Institute of Technology,vol. 12, p. 917-925, Feb. 4, 2010, Mary Ann Liebert, Inc.
Jaafar, Israd et. al., Spectroscopic evaluation, thermal, and thermomechanical characterization of poly(glycerol-sebacate) with variations in curing temperatures and durations, J. Mater Sci, p. 2525-2529, Sep. 13, 2009, Springer Science+Business Media, LLC.
Pryor, Howard et. al., Poly(glycerol sebacate) films prevent post-operative adhesions and allow laparoscopic placement,Surgery, vol. 146, No. 3, p. 490-497, 2009, Boston, MA.
Guo, Xiao-Long et. al., Characterization and optimization of glycerol/sebacate ratio in poly(glycerol-sebacate elastomer for cell culture application, J. Biomed Mater Res Part A, vol. 102A, Issue 11, p. 3903-3907, Nov. 2014, Society for Biomaterials.
Chen, Qi-Zhi et. al., Characterisation of a soft elastomer poly(glycerol sebacate) designed to match the mechanical properties of myocardial tissue, ScienceDirect, p. 47-57, 2008, Biomaterials.

* cited by examiner

*Primary Examiner* — Jeffrey S Lundgren
*Assistant Examiner* — Stephanie K Springer
(74) *Attorney, Agent, or Firm* — McNees Wallace & Nurick LLC

(57) ABSTRACT

A filler material of a thermoset resin of a diacid/polyol, such as PGS is provided. The filler useful in forming composites, such as those in which the filler and a resin matrix are of the same material to provide a homogenous polymeric composition. Composites in which at least one of the matrix, the filler or both are PGS are also provided. Methods of forming such filler materials and composites are also disclosed. The composites allow extrusion process to form articles from materials that would not otherwise be capable of being extruded.

21 Claims, No Drawings

COMPOSITE CONTAINING POLY(GLYCEROL SEBACATE) FILLER

RELATED APPLICATIONS

This application claims the benefit of, and priority to, U.S. App. No. 62/299,595 filed Feb. 25, 2016, and which is hereby incorporated by reference in its entirety.

FIELD

This application relates to composites and more particularly to composites that include glycerol/sebacic acid polymeric filler and to the filler itself.

BACKGROUND

Polymers of glycerol/sebacic acid (PGS), including both homopolymers and copolymers, have been shown to hold great promise as a bioresorbable material for use in medical and other applications. However, PGS has some material drawbacks that have limited potential commercial processing. PGS has a melt temperature of ~35° C. and the curing process to produce the thermoset elastomer requires temperatures above 100° C. Therefore, to produce structures with a defined form a mold is required during the cure process. This limits the potential applications and workable structures of thermoset PGS.

Extrusion is a more desirable way to form shaped goods, but pure PGS cannot be readily extruded due to its low viscosity, non-ideal thermal properties, and long cure times. In order to extrude PGS, it must soften at elevated temperatures to be processed through a dye, outputting a structure that can withstand physiological and/or curing temperatures. Accordingly, extrusion techniques such as electrospinning prove unsatisfactory as it requires co-blending and/or a solvent based extrusion process. In addition, the electrospinning process produces random fiber orientations as opposed to extrusion which produces oriented structures that can be non-fibrous.

SUMMARY

According to an exemplary embodiment, a filler material comprises a thermoset resin of a polymer comprising a condensation reaction product of a diacid and a polyol, the filler material having a particle size between 0.5 and 1000 microns. In some embodiments, the filler material comprises PGS.

According to another exemplary embodiment, an article comprises a composite of a resin matrix and a thermoset filler, the thermoset filler having a particle size between 0.5 and 1000 microns in which the resin matrix, thermoset filler, or both of the resin matrix and thermoset filler comprise PGS and the thermoset filler is present as about 10% by weight to about 90% by weight of the composite.

According to one exemplary embodiment, an article comprises a composite of a thermoset filler having a particle size less than 250 microns in a cross-linked resin matrix in which the resin matrix and thermoset filler both comprise PGS, the thermoset filler is present from about 40% by weight to about 70% by weight of the composite, the resin matrix has a molecular weight of 5,000-50,000 Da. prior to cross-linking, the thermoset filler has a cross-link density of cross-link density of about 0.07 mol/L or greater, and the thermoset filler and the resin matrix each have a molar ratio of glycerol to sebacic acid in the range of 0.7:1 to 1.3:1.

According to another exemplary embodiment, an article comprises a composite of a resin matrix and a thermoset filler, the thermoset filler having a particle size between 0.5 and 1000 microns in which the resin matrix and the thermoset filler both comprise the same material, the thermoset filler being present as about 10% by weight to about 90% by weight of the composite.

According to another exemplary embodiment, a method of forming a filler material comprises providing a thermoset comprising PGS and forming particles of the thermoset material having a particle size between 0.5 and 1000 microns.

According to another exemplary embodiment, a method of forming an article comprises providing a composite comprising a PGS resin matrix and a thermoset PGS filler material having a particle size between 0.5 and 1000 microns, wherein the thermoset PGS filler material is at least 50% by weight of the composite; forming the composite into a predetermined shape; and curing the PGS resin matrix.

Among the advantages of exemplary embodiments are that it has been discovered that with the use of a fine thermoset PGS filler, composite structures can be formed and crosslinked without the need for a mold.

Another advantage is that a composite is provided that includes a matrix and thermoset filler of the same molecular formula, which allows extrusion and other processing of materials that could not be accomplished by the neat resin alone while providing an ability to maintain an article still having an overall homogenous composition.

Another advantage is that PGS resin mixed with PGS filler holds its structure at 37° C. and therefore does not need further processing at high temperatures once the desired structure is formed, but it can still be crosslinked to create a more mechanically stable structure.

Yet another advantage is that composites of PGS resin and PGS filler can be extruded into shapes that hold their geometries at 37° C. and under curing at temperatures above 100° C.

Still another advantage is that in addition to overcoming process difficulties, the ability to extrude PGS in a composite form in accordance with exemplary embodiments opens the potential use of this material to a wider variety of applications, including 3D printing and other additive manufacturing techniques, as well as a wide variety of medical and industrial uses.

DETAILED DESCRIPTION OF EXEMPLARY EMBODIMENTS

Exemplary embodiments are directed to a thermoset PGS filler as well as composites formed using the PGS filler and methods and products related to the same. PGS filler is sometimes referred to herein as a PGS flour or PGS powder.

As used herein, "composite" broadly refers to any combination of a resin and filler material and includes both low and high solids compositions which may be used to form a bulk solid or in coating and film applications, the filler acting as a vehicle-binder adjunct or sole bulk resin to the base formulation. In other embodiments, the filler behaves as an additive with controlled "oil absorption coefficient" action based on particle size such that "wet formulation additives" can adsorb within the filler particles; that is, the filler particles provide a wetting surface to mop up fluid phased additives.

Although described primarily herein with respect to PGS, it will be appreciated that any polymer formed from a multi-functional acid monomer and a polyol monomer capable of forming a thermoset may be employed for forming the filler material. Accordingly, in certain aspects of the invention, the polymer is a condensation reaction product of glycerol or other alcohol monomer and a diacid having the formula [HOOC(CH$_2$)$_n$COOH], wherein n=1-30, including malonic acid, succinic acid, glutaric acid, adipic acid, pimelic acid, suberic acid, and azelaic acid as well as sebacic acid.

Furthermore, although primarily discussed herein with respect to PGS as a preferred resin of the composite, the resins used for the matrix of the composites formed in accordance with exemplary embodiments are not so limited and may be any polymeric material, but preferably are biocompatible and erodible/degradable. Exemplary resins in addition to PGS include a polymer containing glycerol and sebacic acid of varying initial molar ratios, condensation polymers of a diacid (such as those discussed previously) and a polyol, polycaprolactone (PCL), polylactic acid (PLA), polyglycolide (PGA), and poly(glycolide-co-lactide) (PLGA), poly(propylene fumarate), poly(ether esters) such as polydioxanone, poly(ortho esters), polyanhydrides, polycarbonates and co-polymers and blends thereof, as well as suitable urethanes and acrylates. Other suitable resin materials for the matrix include biologics such as, but not limited to, collagen, gelatin, polysaccharides, alginate, glycosaminoglycans, proteoglycans, chitosan and chitin, agarose, etc., which may be used in combination together with and/or blended with one or more of the synthetic resins in the matrix.

According to some presently preferred embodiments, the composite is formed of a resin and a thermoset filler having the same chemistry.

The matrix resin should be able to flow or soften at a given temperature to allow for particle integration. Particularly in the case where the resin is PGS, the PGS resin has a molecular weight in the range of 5,000-50,000 Da; in some embodiments, the PGS resin has a molecular weight in the range of 15,000-25,000 Da. References herein to molecular weight refer to weight average molecular weight.

The matrix may be composed entirely of the polymer resin or may include one or more additional components. In some embodiments, the matrix contains one or more drugs, medicaments, or other biologically and/or pharmaceutically active ingredients which may be incorporated therein for controlled release during subsequent resorption or degradation of the matrix due to PGS' surface eroding characteristics.

The filler of the composites in accordance with exemplary embodiments comprises thermoset PGS (or other polymer of a diacid and polyol) that has been processed into a flour or powder of fine particle size (e.g., less than 1000 microns). The PGS thermoset filler cross-link density is about 0.07 mol/L or greater, which is calculated with respect to the thermoset material prior to particularization by soaking samples in tetrahydrofuran for 24 hours to obtain a swollen mass, dried until a constant dry mass is acquired (typically about 3 days) and the swelling percentage is then used to calculate the crosslink density using the Flory-Rehner expression for tetra-functional affine networks.

The success of using PGS as a filler material was unexpected and surprising; PGS is a soft elastomer and thus would not ordinarily be considered a suitable filler material in many applications, particularly for dispersion within a matrix comprising PGS resin to form a composite that demonstrates significant differences in rheology and improved handling and processing characteristics over either neat PGS resin or neat thermoset PGS alone.

Other materials, both organic and inorganic, may be used in combination with PGS flour as an additional filler material for forming composites in accordance with exemplary embodiments and include particles of collagen, inorganic salts (e.g. calcium phosphate, titanium dioxide), gelatin, PCL, PGLA, PGA and PLA, all by way of example only. Even if other fillers are used, the PGS filler should remain the primary filler component to create a stable composite with a rheology that can maintain its structure at physiological 37° C., as well as at curing temperatures above 100° C.

Filler particle size may vary depending on application, but the filler is generally between 0.5 and 1000 microns and typically less than 850 microns. Smaller particle sizes are generally preferred for additive manufacturing and traditional Brabender or fiber extrusion machines, with comparatively larger sizes being able to be used for industrial, orthopedic, wound care and dental applications. In some embodiments, maximum particle size is about 60 to 125 microns for additive manufacturing, while maximum particle size for other forms of extrusion is typically in the range of about 75 to about 300 microns, such as about 175 to about 250 microns.

The thermoset filler can be manufactured by any suitable method of forming fine particles of thermoset material.

In one embodiment, thermoset PGS is processed into filler particles by cryogrinding. In this process, a sheet or other larger mass of thermoset PGS is frozen to very low temperatures, e.g. direct exposure to liquid nitrogen. This renders the PGS thermoset brittle enough to be ground into small granules while in its frozen state. The thus-formed filler particles resume their elastomeric state upon returning to ambient temperature after completion of the process. Cryogrinding may be most useful when filler particles having smaller diameters (e.g. about 300 microns or less) are desired.

In another embodiment, the filler particles are formed through an extraction and milling technique. PGS can be analogized to a sol-gel, with higher molecular weight chains acting as the gel and lower molecular weight chains acting as the connective sol. When thermoset PGS is soaked in an organic solvent, some sol portions are removed, which results in an unstable structure of gel portions capable of being ground into a fine powder.

In the extraction process of PGS filler manufacture, thermoset PGS is soaked in an organic solvent (such as ethyl acetate or THF) which dissolves a portion of the low molecular weight fractions of the PGS. This weakens the overall thermoset structure and allows it to crumble when agitated, such as with a dual-asymmetric centrifuge mixer, resulting in a fluffy powder-like material.

In some embodiments, ethyl acetate is a preferred organic solvent, as it has demonstrated better selectivity in dissolving low molecular weight fractions. Other organic solvents, such as THF, may also be used but can tend to also pull out some higher molecular weight fractions. The removal of some higher molecular weight fractions may be desired in some cases to produce smaller particle sizes. Particle size can be controlled based on solvent soak time, with longer soaks and/or removal of higher molecular weight fractions resulting in smaller particle sizes, as well as the glycerol to sebacic acid molar ratio used in the polymerization of PGS.

Regardless of the technique used, the resulting filler particles can then be further sized, for example, by sieving or other sizing techniques. The PGS filler particles are observed to be cohesive and tend to agglomerate. Accordingly, in some embodiments the filler particles can be wetted with ethyl acetate to reduce particle interaction as well as provide additional weight. Hydroxyapatite can also be used to prevent particle interactions by coating the particles, minimizing any interactions and resulting in a fine powder. In another embodiment, sizing may occur while the particles are in a harder, frozen state, such as under the presence of liquid nitrogen.

The molar ratio of glycerol:sebacic acid in the thermoset PGS used for the filler material may vary, but typically is in the range of 0.7:1 to 1.3:1. Reducing the amount of glycerol relative to the amount of sebacic acid produces a larger amount of finer particle sizes during filler particle production using the extraction method due to a smaller percentage of sol holding the structure together. However, higher amounts of glycerol, for example, up to 1.3:1 glycerol:sebacic acid, is also suitable, with a preference in some embodiments for a 1:1 molar ratio. While the stoichiometric ratios of glycerol to sebacic acid can be varied for the PGS particles, the particles should still be of a surface energy similar to that of the resin matrix. In some embodiments, that is accomplished by providing the PGS filler particles having a molar ratio of glycerol:sebacic acid that is similar or the same as that of the resin in the matrix. In a presently preferred embodiment, a composite includes a PGS thermoset filler made from 1:1 glycerol:sebacic acid molar ratio dispersed in a PGS resin matrix that also has a 1:1 glycerol:sebacic acid molar ratio.

Like the matrix material, the polymeric material used to form the filler particles may be doped with an active ingredient.

The filler particles are added to the resin matrix to form a composite. The weight percentage of filler in the composite may vary widely based on numerous factors, including the intended end use application. Generally, the composite is about 10% by weight to about 90% by weight filler. In some embodiments, the composite is about 40% by weight to about 70% by weight filler for extrusion applications, preferably at least 50% by weight or more filler (for 75-250 μm particles), in order for the composite to hold its shape. It has been observed that higher ratios of filler result in increases in peak load of the final cured composite and enhanced mechanical integrity in the uncured composite. Further as previously noted, to the extent that the filler particles include multiple different materials, the filler should be primarily the particulate thermoset material, which is preferably of the same composition used as the resin matrix.

By outward appearances, the composite appears to cure at room temperature, as the composite hardens and does not exhibit the tackiness or stickiness associated with uncured PGS resin at that temperature. Despite the appearance, analysis by differential scanning calorimetry reflects that the composite does not cure at room temperature, although it does suggest the filler influences the crystallization temperature of the resin, shifting it lower. While the filler does not apparently alter the cure itself, it does render a composite that is capable of holding its shape and which can be readily handled. While not wishing to be bound by theory, it is believed that some of the morphology changes result from the filler particles absorbing or adsorbing the uncured resin of the composite.

The composite can be processed and shaped in any desired fashion, including by extrusion into tubes, fibers, or other devices and/or as an ink for use in additive manufacturing. In some cases, the composite may be compounded and/or co-extruded with other polymeric materials.

Once the desired shape is formed, the composite can be cured into the final product without the use of a mold. Curing the composite (i.e., curing the resin matrix of the composite) typically takes place at temperatures in excess of 100° C. under pressures less than atmospheric pressure and results in a final product formed of the composite material. In some embodiments, the curing step may also involve annealing. In some embodiments, the composite is cured at a temperature of about 90° C. to about 150° C. at a pressure in the range of about 5 torr to about 20 torr for a period of about 4 hours to about 96 hours.

Like neat PGS, a PGS/PGS composite has a controlled release due to surface erosion of both the resin matrix and thermoset particles. The resin and thermoset particles of the composite have different crosslink densities and, as a result, degrade at two different rates. in vitro degradation studies of different PGS/PGS composite structures closely mimicked cast PGS thermosets with an initial bolus degradation, followed by a linear decrease in mass loss over time. Surface erosion was also confirmed by surface topography analysis over time, as well as inherent pore formation limited to the surface. in vivo, composites in accordance with exemplary embodiments may form a porous network in real time as the resin portion of the composite degrades faster than the thermoset particles allowing for cellular infiltration into the composite structure.

Like neat PGS, exemplary embodiments also exhibit antimicrobial activity and composites can be used in suitable applications for that purpose. In one embodiment, the composite is a delivery vehicle for controlled release or dual controlled release whereby the degradative action of the polymer of the composite releases an included (by formulation) bioactive material with a specified or tailored release profile, as well as the underlying anti-microbial degradation products of the PGS components themselves.

Exemplary embodiments may be employed in any situation for which it is desirable to provide a resorbable composite polymer with antimicrobial benefits. Exemplary applications include agriculture; construction; water management; surface preservation; architectural preservation; anti-fouling; environmental barriers; wound healing fabric surfaces, treatments, coatings, and controlled release vehicles; food additive; biomedical device coating/adhesive/sheets or films for implant device prophylactic peri-operative post-surgical infection control; temporary barriers; any surface where microbial colonization threatens human health or condition; hydrophilic agents; textile treatments; veterinary; wound care; biofilm control; regenerative engineering without antibiotic need; surface protection sanitization; water management; filtration; fabric coating for protection; implantable textiles; prophylactic prosthetic implant coatings; conformal coatings; cosmetics; OTC pharma; and aquaculture, all by way of example only.

PGS composites in accordance with exemplary embodiments can be integrated into a wide variety of textile structures. Textile structures can be made from monofilament or multifilament yarn comprising, without limitation, polylactides and polyglycolides and their copolymers, polydioxanone, polytrimethylene carbonate, polycaprolactone, polyethylene terephthalate, low to ultra-high molecular weight polyethylene, polypropylene, polyamides, silk, and polytetrafluoroethylene. Cured tube or rod composites of varying sizes can be placed on mandrels and braided over. Uncured composite sheets can also be softened using higher temperatures and laminated with meshes of different polymer types and constructions using a die press, 3-roll-stack, or other laminating techniques. These laminated sheets can then be cured to form one cohesive structure that is unable to be delaminated. PGS composites can also be co-extruded with textile structures that nullify the need for a subsequent lamination step. PGS composites reinforced with textiles can be constructed into medical devices for use as, but not limited to, cardiovascular patch, cardiac patch, pericardial patch, cardiac support mesh wrap, vessel guard, vascular graft, shunt, adhesion barrier, dural substitute, nerve conduit, heart valve, pacemaker mesh bag, tympanostomy tube, annuloplasty ring, meniscal scaffold, bone sheath or wrap, tendon wrap, surgical film, or surgical mesh.

Among the applications for which exemplary embodiments of the invention may be employed include a wide variety of medical and industrial applications. In some embodiments, the composite may be used in the creation of an implant, or as a lubricant or coating on implants or other devices used in orthopedic, neural, and cardiovascular applications, for example. Other medical applications include use in wound care such as the formation of a composite of a collagen flour (e.g. Avitene) and PGS thermoset filler to form a hydrogel, bone putty composites (PGS resin, calcium phosphate and PGS thermoset filler), and bone plugs formed of cured putty cut to a variety of different sizes.

Still other medical applications include a vehicle for delivery of substances by subcutaneous injection, two-part drug delivery, and as a porogen, all by way of example.

Industrial applications include use in degradable paints and inks; food processing to deliver flavor or vitamins; water treatment such as for controlled release of algaecide, pesticide or other treatments; or even as delayed release fish food, again all by way of example.

EXAMPLES

The invention is further described with respect to the following examples which are presented by way of exemplification and not limitation.

Example 1

PGS/PGS composites were formed by using a PGS thermoset filler added to a PGS resin at various loading levels. The filler was created by the extraction method described herein starting with a PGS thermoset having a cross-link density greater than 0.100 mol/L (prior to particle formation) to provide a PGS thermoset filler having an average particle size less than 212 µm. The filler was added into a PGS resin (MW 12,625, PDI 7.044), in amounts of 50%, 60% and 70% by weight, and pressed into a 1 mm film followed by curing at 20 hours at 120° C. at a pressure of 10 torr.

Tensile testing of the resulting specimens was conducted and reflected that increasing filler concentration led to an observed increase of Young's Module (up to 800 kPa) and a decreased strain at break from 0.5 to 0.3. The composites also showed an increased suture strength compared to a cast film of neat PGS. While suture strength of cast films is typically less than 1.5N, the lowest suture strength observed for the cured PGS composites of Example 1 was almost 50% higher at 2.2N.

Example 2

To explore applicability for orthopedic applications, PGS fillers (<212 µm particle size, MW 21,597 of resin prior crosslinking, cross-link density greater than 0.100 mol/L and glycerol:sebacic acid ratio (1:1)) were mixed with varying amounts (3%-25% wt) of hydroxyapatite (HA), which formed finely coated, discrete PGS filler particles. Composites of PGS filler, PGS resin (also having a 1:1 glycerol: sebacic acid ratio) and a calcium phosphate filler (including hydroxyapatite (HA) and β-Tricalcium phosphate (TCP)) were formed into a moldable paste.

A variety of composites were formed including: Ex. 2a.: 30% wt PGS flour (212-850 µm), 30% wt HA and 40% wt PGS resin; Ex. 2b.: 35% wt PGS flour (<212 µm), 20% wt HA and 45% wt PGS resin; Ex. 2c.: 50% wt. PGS flour (212-850 µm), 30% wt TCP and 20% PGS resin; and Ex. 2d.: 40% wt PGS flour (<212 µm), 30% wt TCP and 30% wt PGS resin.

Example 3

PGS/PGS composites of different weight ratios were extruded through a 965 µm nozzle with a dispenser to explore applicability for 3D printing applications. Compositions with a 40% wt filler concentration showed the most promise, with a structure that was fairly maintained after curing; those at less than 40% by weight did not hold their shape well; those in excess of 40% wt, up to 70% wt, provided suitable in maintaining structure but with increasing viscosity and slower to extrude. Filler particles can be pre-wetted with glycerol or oil to minimize the hardening and subsequent extrusion difficulties associated.

Example 4

Vitamin $B_{12}$ was loaded at 3% w/w concentration into PGS resin. The material was cured at 120° C. for 48 hours. The resulting thermoset was formed into filler particles by the extraction method. Approximately 100 mg of the particles were placed into multiple vials and soaked in phosphate buffered saline (PBS) of pH=7.4. At predetermined incubation times the PBS of the samples was tested by UV/Vis to determine the amount of Vitamin $B_{12}$ released, and the mass loss of the sample was also determined. The rate of vitamin $B_{12}$ release and mass loss both exhibited a linear trend (5.95 µg/day and 0.16%/day respectively), indicating the filler exhibits controlled release properties due to its surface degradation mechanism.

To demonstrate a 2-part controlled release mechanism for actives, curcumin-doped PGS flour particles were combined with PGS resin (containing 5% w/w Vitamin $B_{12}$) in a 60:40 ratio by mixing 200 g of the doped resin with 300 g of the doped flour particles to create a composite. The glycerol: sebacic acid molar ratio for each of the flour particles and the resin matrix was 1:1. Samples were cured at 120° C. and 10 Torr for a 15 hour period and cut into 1 mm wafers. The samples were placed into individual vials and soaked in phosphate buffered saline (PBS) of pH=7.4. At predetermined incubation times the PBS of the samples was tested by UV/Vis to determine the amount of Vitamin $B_{12}$ and curcumin released. Results demonstrated zero-order release of both $B_{12}$ (1.2%/day) and curcumin (0.12%/day) at different rates. The two different linear release rates are due to the difference in crosslink density between the resin portion (lower crosslink density) of the composite and the flour particles (higher crosslink density).

Example 5

A 1 mm PGS thermoset was made by casting and curing molten PGS in a mold, which took approximately 72 hours to cure. A PGS/PGS composite (60% wt. PGS flour to 40% wt. PGS resin—each of a 1:1 glycerol:sebacic acid molar ratio) of the same size was manually formed into a block without a mold and held its shape during curing. This exhibited a full cure in 15 hours, illustrating the same final dimension of PGS in thermoset form can be manufactured in less than half the time with the PGS/PGS composite compared to the PGS resin. This is believed to at least partly result from the decreased PGS resin present in the PGS/PGS composite. The PGS resin appears to thinly coat the thermoset filler particles, with the thin PGS resin film curing faster than a thick layer of PGS resin.

Example 6

A PGS flour/PGS resin 60/40 w/w ratio (each a 1:1 molar ratio of glycerol:sebacic acid) was injected into a Brabender at 10 mL/min with a syringe pump. After approximately 50 g of material had traveled through the screw, a hollow tube was successfully extruded through a 0.5 inch OD×0.25 inch ID tube die. The same composite was successfully extruded in the same manner through a 0.375 inch OD×0.125 inch ID tube die. A select amount of the tubing was cured in the oven at 120° C. and 10 Torr for approximately 16 hours. The tube held its shape in the oven and the inner wall thickness showed minimal change.

This same PGS flour/PGS resin 60/40 w/w ratio was injected with an air cylinder into the Brabender and extruded into a variety of shapes/sizes using different dies. Sheets, tubes and rods were all successfully extruded on a commercial scale, with types and sizes of materials outlined in Table 1. All shapes were further processed by curing in a vacuum oven at 120° C., 10 torr for a minimum of 15 hours and a maximum of 48 hours. Shapes maintained their structure through the curing process.

TABLE 1

| Sheet | Tube | Rod |
| --- | --- | --- |
| 1 mm | 2.5 mm OD, 1.5 mm ID | 1 mm dia |
| 500 µm | 3 mm OD, 2 mm ID | 3 mm dia |
|  | 5 mm OD, 3 mm ID |  |
|  | ¼" OD, ⅛" ID |  |
|  | 9 mm OD, 6 mm ID |  |
|  | ⅜" OD, ¼" ID |  |

Example 7

Porous structures were also achieved with a salt leaching technique. A 55/45 PGS flour/resin ratio and 2:1 salt:resin of salt/PGS resin/PGS flour mixture was injected into the brabender twin screw extruder and processed like the neat composite structures. A salt composite 1 mm sheet and ⅜" OD ⅛" ID tube have successfully been extruded, cured and then soaked in water to remove salt leaving open pores.

Example 8

Calcium chloride, sodium chloride and PGS flour were processed to obtain particles having an average particle size less than 106 µm. A 50% by weight filler to PGS resin composite was mixed and formed into a sphere. The spheres were cured at 120° C. and 10 Torr for approximately 16 hours. Among the different fillers of the same particle size, the PGS/PGS composite was the only one to maintain the spherical shape. Through SEM imaging, PGS filler particles were fully integrated, while NaCl particles appeared to repel the PGS and $CaCl_2$ appeared to have coated the outer surface of the particle suggesting that particle size alone is not sufficient for composite formation and that chemical compatibility between resin matrix and flour is necessary for successful composite formation.

Example 9

PGS filler particle size was varied (<212 µm, 212-850 µm, and 1-2 mm) and used to make 60% by weight PGS filler to PGS resin composites. Rheology of the uncured composites showed similar LVE ranges, indicating stable structures. The samples were cured into spheres, in which only the smallest PGS flour particles (e.g. <212 µm) maintained a spherical shape. However, all PGS/PGS composites were homogeneous and flexible structures. A 400 µm gelatin/PGS resin composite of the same ratio was also constructed; it's rheology showed a very short LVE range, representative of an unstable structure. After curing, the hard, brittle gelatin/PGS composite did not maintain its shape.

Example 10

PGS/PGS composite extruded tubes of sizes 0.25 inch OD, 0.125 inch ID and 3 mm OD, 2 mm ID were placed onto an appropriate sized mandrel and assembled to be fed into a braider. PGA fiber was used to create a braid over top of the extruded tubes and suture retention of the structure increased. PGS/PGS composites were also incorporated into textiles by laminating using mild temperatures and a press to secure uncured extruded sheet onto low and high porosity meshes made from PET, PGA, and PP.

Example 11

PGS composites were tested for antimicrobial activity and efficacy against *Pseudomonas aeruginosa* and *Staphylococcus aureus*. Surfaces of PGS composites were inoculated with bacteria and compared against polypropylene controls. After a 24-hour incubation time, PGS composites demonstrated >6.38 and >5.80 log reduction against *Pseudomonas aeruginosa* and *Staphylococcus aureus* which equates to >99.99996% and >99.9998% reduction in bacterial counts, respectively.

Example 12

PGS flour particles of <212 um size were formulated with a gelatin PGS mixture as described in U.S. Pub. No. 20160046832 in a 60:40 ratio by mass using dual-asymmetric centrifuge mixing. The resultant composite was pressed into a 1 mm film and lyophilized for a 16-hour period. The lyophilized film exhibited good mechanical strength and was porous. The film was then further processed in a vacuum oven at 120° C. and 10 Torr for a 15-hour period to produce a film that could withstand aqueous in vivo conditions. Such a film could act as a wound care dressing or soft tissue filler.

Example 13

PGS flour/resin (60/40 wt./wt.) were extruded into 3 mm rod; 0.25 inch OD, 0.125 inch ID tube; and 1 mm sheet. Samples were cured for 15 or 24 hours. Once cured, samples were cut to 2" length (tube and rod) or ASTM D638-V dog-bone (sheet). Samples were soaked in 0.05M PBS at pH=7.4 and 37.0° C. for predetermined amounts of time. Samples were analyzed for mass loss, changes in surface morphology (SEM), and mechanical strength (rod and sheet for tensile, tube for compression) over time. All three sample types showed a linear relationship ($R^2$ values >0.99)

between mass loss and degradation rate, indicating they degrade by surface erosion. Furthermore, mechanical testing showed a linear loss of mechanical strength, whether tensile or compression, over time. Scanning electron microscopy revealed the formation of pores over time that are limited to the surface of the sample, further indicating the sample degrade by surface erosion. These results verify that PGS/PGS composites maintain the surface erosion characteristic of a neat, homogenous PGS material.

Example 14

A 60/40 w/w flour to resin extruded 1 mm sheet composite was tested in an intramuscular in vivo rabbit model. Twelve female New Zealand White rabbits underwent anesthesia to expose the paravertebral muscle. Three pockets per animal were formed between the muscle fibers. Gamma sterilized 10×1×1 mm composite, steam sterilized 10×1×mm high density polyethylene (HDPE) (negative control) and 10 mm long Vicryl PGA suture (positive control) were implanted into the pockets along with location markers. The fascia was closed with nonabsorbable suture and the skin was closed with stainless steel wound clips. Animals were housed in an AAALAC International accredited facility and room temperature, relative humidity, light cycle, and general health were maintained/observed daily.

At 2, 4, 8 and 16 weeks after implantation, three animals were arbitrarily selected, euthanized and paravertebral muscles were dissected and fixed in buffered formalin. The composite test article showed near complete or complete degradation at weeks 4, 8 and 16. It was a slight irritant compared to HDPE at week 2, and a non-irritant compared to HDPE at weeks 4, 8 and 16. Compared to the Vicryl PGA suture, the PGS composite was a non-irritant at all time points.

Example 15

A poly(glycerol sebacate) urethane (PGSU) was produced by reacting an oligomeric form of PGS with HDI in a ratio of 1:1 HDI:free hydroxyl. Resultant material was a thermoset urethane. Material was to ground to achieve sub-212 micron particles using a dual-asymmetric centrifugal mixer. PGSU flour particles resembled standard PGS flour particles in terms of consistency and particle shape. PGSU flour particles could be formulated with PGS resin in a 60/40 flour/resin ratio to obtain a stable composite.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departure from the scope and spirit of the appended claims.

Moreover, as used herein, the term "about" means that dimensions, sizes, formulations, parameters, shapes and other quantities and characteristics are not and need not be exact, but may be approximate and/or larger or smaller, as desired, reflecting tolerances, conversion factors, rounding off, measurement error and the like, and other factors known to those of skill in the art. In general, a dimension, size, formulation, parameter, shape or other quantity or characteristic is "about" or "approximate" whether or not expressly stated to be such. It is noted that embodiments of very different sizes, shapes and dimensions may employ the described arrangements.

Furthermore, the transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinary associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of" and consisting of."

What is claimed is:

1. An article comprising a composite of a matrix formed of a polymer resin and a thermoset filler, the thermoset filler in a thermoset state being mixed with the polymer resin in an uncured state to form the composite, the thermoset filler having a particle size between 0.5 and 1000 microns, wherein the polymer resin, thermoset filler, or both of the polymer resin and thermoset filler comprise polymer of glycerol/sebacic acid (PGS), the thermoset filler being present as about 10% by weight to about 90% by weight of the composite.

2. The article of claim 1, wherein the polymer resin is in a cured state.

3. The article of claim 1, wherein the polymer resin has a weight average molecular weight of 5,000-50,000 Da prior to crosslinking.

4. The article of claim 3, wherein the thermoset filler has a cross-link density of about 0.07 mol/L or greater.

5. The article of claim 1, wherein the thermoset filler comprises PGS.

6. The article of claim 5, wherein the polymer resin comprises PGS.

7. The article of claim 6, wherein the thermoset filler and the polymer resin each have a molar ratio of glycerol to sebacic acid in the range of 0.7:1 to 1.3:1.

8. The article of claim 7, wherein the thermoset filler and the polymer resin each have the same molar ratio of glycerol to sebacic acid.

9. The article of claim 7, wherein the molar ratio of glycerol to sebacic acid is 1:1.

10. The article of claim 1, wherein the composite exhibits antimicrobial activity based on the presence of the PGS.

11. The article of claim 1, wherein the polymer resin comprises polycaprolactone (PCL), polylactic acid (PLA), polyglycolide (PGA), poly(glycolide-co-lactide) (PLGA), poly(propylene fumarate), poly(ether esters), polydioxanone, poly(ortho esters), polyanhydrides, polycarbonates, co-polymers thereof, blends thereof, urethanes, acrylates, collagen, gelatin, polysaccharides, alginate, glycosaminoglycans, proteoglycans, chitosan, chitin, or agarose.

12. The article of claim 1 further comprising a second filler selected from the group consisting of inorganic salts, calcium phosphate, hydroxyapatite, β-Tricalcium phosphate, titanium dioxide, collagen, gelatin, PCL, PGLA, PGA, PLA and combinations thereof.

13. The article of claim 1, wherein the composite comprises at least 50% of the thermoset filler, by weight, based on a total weight of the composite.

14. The article of claim 1, wherein the PGS is doped with an active ingredient.

15. The article of claim 1, wherein the particle size of the thermoset filler is less than 300 microns.

16. An article comprising a composite of a thermoset filler having a particle size of at least 0.5 microns and less than 250 microns in a cross-linked matrix formed of a polymer resin, the thermoset filler in a thermoset state being mixed with the polymer resin in an uncured state to form the composite, wherein the polymer resin and the thermoset filler both comprise polymer of glycerol/sebacic acid (PGS), the thermoset filler is present from about 40% by weight to about 70% by weight of the composite, the polymer resin has a molecular weight of 5,000-50,000 Da. prior to cross-linking, the thermoset filler has a cross-link density of about 0.07 mol/L or greater, and the thermoset filler and the polymer resin each have a molar ratio of glycerol to sebacic acid in the range of 0.7:1 to 1.3:1.

17. A method of forming an article comprising:
providing a composite comprising a matrix formed of a polymer resin and a thermoset filler having a particle size between 0.5 and 1000 microns, the thermoset filler in a thermoset state being mixed with the polymer resin in an uncured state to form the composite, wherein the polymer resin and the thermoset filler comprise polymer of glycerol/sebacic acid (PGS), the thermoset filler being present as 50% to about 90% by weight of the composite;
forming the composite into a predetermined shape; and
curing the polymer resin.

18. The method of claim 17, wherein the step of forming comprises extruding.

19. The method of claim 17, wherein the step of curing is carried out in the absence of a mold at temperatures in the range of 90° C. to 150° C. at less than atmospheric pressure.

20. The article of claim 1, wherein the article is an adhesion barrier, the article further comprising a textile, the textile reinforcing the composite.

21. The article of claim 1, wherein the article comprises an adhesion barrier.

* * * * *